United States Patent [19]

De Lange

[11] Patent Number: 5,115,460

[45] Date of Patent: May 19, 1992

[54] X-RAY ANALYSIS APPARATUS COMPRISING AN ADJUSTABLE SLIT DIAPHRAGM

[75] Inventor: Roelof De Lange, Almelo, Netherlands

[73] Assignee: U.S. Philips Corp., New York, N.Y.

[21] Appl. No.: 626,085

[22] Filed: Dec. 11, 1990

[30] Foreign Application Priority Data

Dec. 12, 1989 [NL] Netherlands .......................... 8903044

[51] Int. Cl.⁵ ......................... G01N 23/20; G21K 1/04
[52] U.S. Cl. ..................................... 378/150; 378/81; 378/153
[58] Field of Search ............... 378/145, 146, 147, 150, 378/151, 152, 153, 79, 81

[56] References Cited

U.S. PATENT DOCUMENTS

| | | | |
|---|---|---|---|
| 3,852,594 | 12/1974 | Paolini | 378/81 |
| 4,380,820 | 4/1983 | Cutter | 378/153 |
| 4,466,112 | 8/1984 | Covic et al. | 378/150 |
| 4,535,469 | 8/1985 | Brandt | 378/153 |

Primary Examiner—Janice A. Howell
Assistant Examiner—David P. Porta
Attorney, Agent, or Firm—William L. Botjer

[57] ABSTRACT

An X-ray analysis apparatus comprises an adjustable entrance slit which consists of two laminations which are rotatable about axes extending parallel to a $\theta$-axis. By choosing the radius of the laminations and their position in the X-ray beam, a substantially more accurate adjustment can be achieved notably for small $\theta$-values. Moreover, asymmetry in the beam path can be simply compensated for and improved shielding against scattered radiation is achieved.

11 Claims, 2 Drawing Sheets

X-RAY ANALYSIS APPARATUS COMPRISING AN ADJUSTABLE SLIT DIAPHRAGM

BACKGROUND OF THE INVENTION

The invention relates to an X-ray analysis apparatus, comprising an X-ray source, an adjustable divergence slit, an angle adjusting mechanism for rotating an object about a $\theta$-axis, and an X-ray detector.

An X-ray analysis apparatus of this kind is known from U.S. Pat. No. 4,535,469. An entrance in an apparatus described therein is formed by a rotatable slit diaphragm, the rotation of the diaphragm being coupled to a $\theta$-axis rotation for an object to be examined. It is the object to keep the dimensions of an irradiated object surface constant as the $\theta$-position changes. Such an adjustable divergence slit offers a substantial improvement, but usually causes an increase of scattered radiation which arises at boundaries of the diaphragm. Furthermore, for comparatively small values of the $\theta$-angle, the slit device becomes too inaccurate.

SUMMARY OF THE INVENTION

It is an object of the invention to mitigate said drawbacks; to achieve this, an X-ray analysis apparatus of the kind set forth in accordance with the invention is characterized in that the adjustable divergence slit comprises two X-ray absorbing laminations which are situated on envelopes of cylinder so as to be rotatable about axes extending parallel to the $\theta$-axis of a goniometer.

The construction using two rotatable laminations enables accurate adjustment to be achieved also for comparatively small $\theta$-values, and the scattered radiation can be substantially reduced at the same time.

The laminations in a preferred embodiment constitute mutually identical segments of cylinders whose axes are situated at a distance which is substantially equal to the cylinder radius, measured from a radiation vector between a center of the radiation source and a central point of an object to be irradiated. The two laminations are notably rotatable at the same angular speed. Preferably, a convex side of a first lamination which is situated outside the angle enclosed by the radiation vector and the diffracted radiation vector faces the source and the concave side of a second lamination which is situated therewithin faces the source. The scattered radiation from the boundary of the former lamination is thus substantially intercepted by the second lamination. Scattered radiation from the second lamination extends mainly outside a detection aperture of the apparatus, so that it does not have a signal-disturbing effect.

For optimum adaptation to a surface to be irradiated, independent control of the two rotations may be advantageous. Asymmetrical irradiation of the object is then also possible and correction can be made for a difference in distance, measured across the surface of the object, from the radiation source. The rotations are correlated to the $\theta$-rotation, but are preferably not mechanically coupled thereto.

The construction of a further preferred embodiment is such that the angular speed for the laminations deviates from the $\theta$-angle adjustment, and by selection of the radius of the laminations it can be achieved that for comparatively small $\theta$-values a specimen tilt of $\alpha°$ requires a lamination rotation of, for example 10 $\alpha°$. This geometry can be realized in that the slit is adjusted for a minimum width in said orientation and in that for the shielding lamination boundaries rotation of the laminations results mainly in a translation in the radiation vector direction.

If a facility for complete closure is also required, the laminations may be constructed so as to overlap one another radially. To this end one of the laminations may also be provided with a cut-out, the cooperating lamination being provided with a mating raised portion. The rotation of the two laminations should be synchronous along a final path in the latter case.

In a further preferred embodiment, the diaphragm is formed by two laminations, a first lamination being journalled about a shaft which is stationary with respect to a housing, a second lamination being journalled about a second shaft which is resiliently coupled thereto. As a result, suitable parallelism of the two shafts and accurate spacing from one another can be ensured.

Preferably, the two laminations are separately driven by an encoded motor, coupling between the two drives, if any, taking place via encoding. The drive motors are, for example step motors or DC motors provided with encoders, so that they are not mechanically coupled, even though this is possible. Similarly, the drives may be coupled in an encoded fashion to a drive motor for the object, so to the $\theta$-angle adjustment, and possibly also to a drive for an adjustable exit slit. Because of the possibility of improved scattered radiation interception in the entrance slit, however, an exit slit can then be more readily dispensed with. In cases where an exit slit serves as a radiation shield, its construction may be simpler and it may comprise, for example a single drive motor.

BRIEF DESCRIPTION OF THE PREFERRED EMBODIMENTS

Some preferred embodiments in accordance with the invention will be described in detail hereinafter with reference to the drawing. Therein:

FIG. 1 diagrammatically shows an X-ray analysis apparatus in accordance with the invention, FIG. 2 shows an example of the beam path via a relevant adjustable entrance slit, and FIG. 3 diagrammatically shows the construction of an adjustable slit diaphragm.

DETAILED DESCRIPTION OF THE PREFERRED EMBODIMENTS

Figure 1:
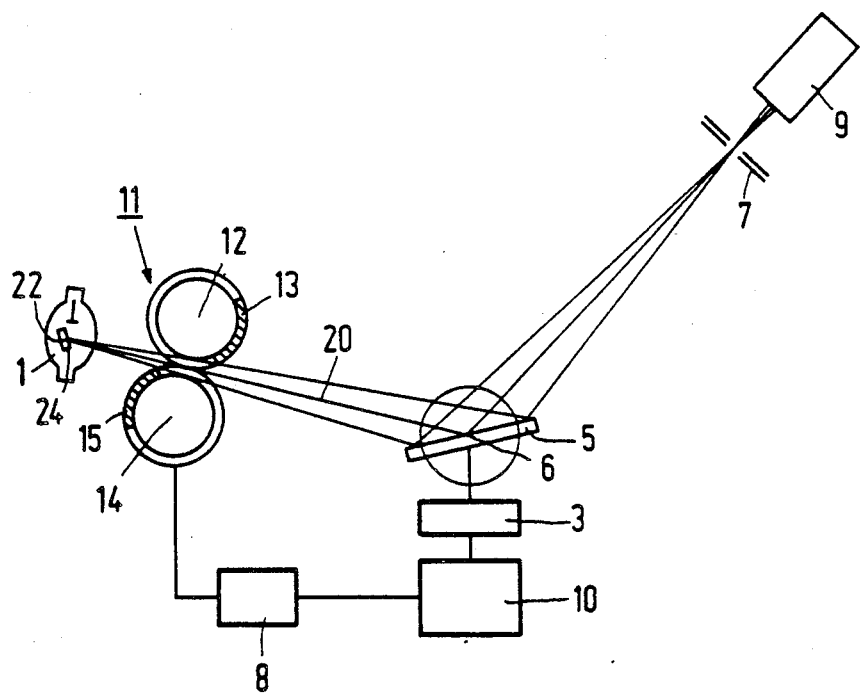

An X-ray analysis apparatus as shown in FIG. 1 comprises an X-ray source 1, an object 5 which is arranged on a goniometer 3, and an X-ray detector 9 which is in this case provided with a detector entrance slit 7. The object can be rotated about a $\theta$-axis 6 by means of the goniometer. The X-ray source 1 is, for example an X-ray tube, the object being a specimen or a monochromator crystal to be analyzed; the X-ray detector may be formed by a scintillation detector, a gas ionization detector, a combination thereof or possibly by a multichannel position-sensitive semiconductor detector.

Between the X-ray source 1 and the object 5 there is situated an adjustable divergence slit 11 which is formed in accordance with the invention by a lamination 13 which is rotatable about a shaft 12 and a lamination 15 which is rotatable about a shaft 14. The shafts 12 and 14 extend parallel to one another and parallel to the $\theta$-axis 6, and hence perpendicularly to a radiation vector 20 and parallel to an object surface to be irradiated. The laminations 13 and 15 constitute parts of cylinders which have, for example a radius of approximately 5 mm and a length of approximately 10 mm and extend, for example, from 120° to 180° about the shafts 12 and 14. The laminations are preferably made of a material having a comparatively high X-ray absorption, for example brass, chromium, tungsten and the like. A portion 19 of an X-ray beam 18 to be emitted by the X-ray source 1 is transmitted in the position of the diaphragm shown (see also FIG. 2). Starting from a focus or radiation object 22 on an anode 24 of the X-ray tube, the X-ray beam is in this case substantially symmetrical about the radiation vector 20 which connects a center of the focus to a center of the object. However, the beam may also deviate substantially from said symmetry. The focus, and hence the X-ray beam, is linear in practical cases with a longitudinal axis extending perpendicularly to the plane of drawing. Movements in the goniometer and for the slits can be executed by a motor-drive system 8 controlled by a control mechanism 10.

Figure 2:
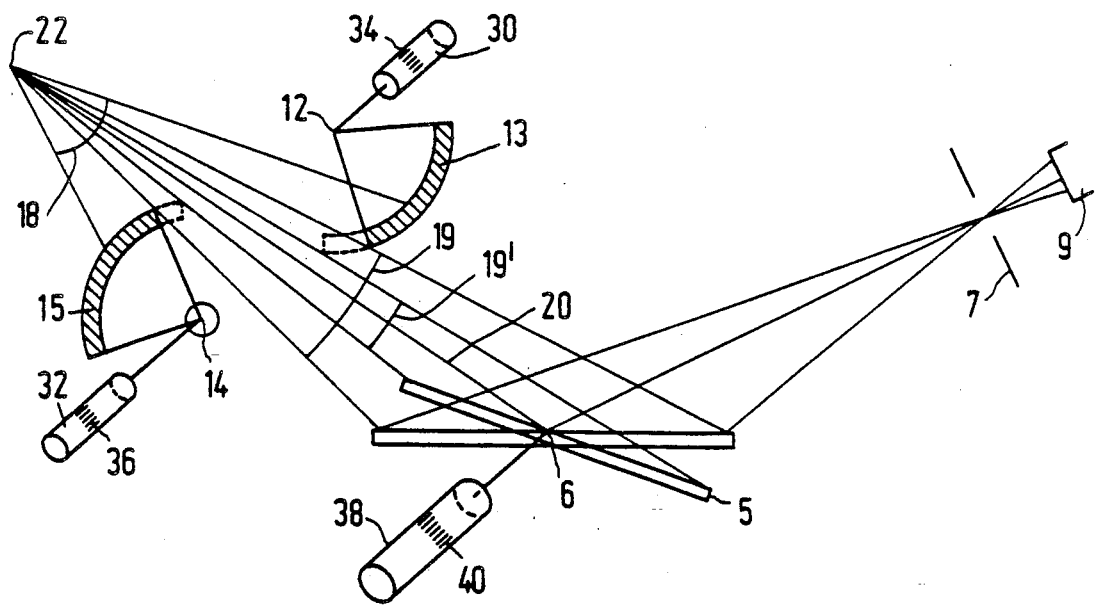

Interrupted lines in FIG. 2 denote a radiation beam for a smaller angle of incidence $\theta$ where the diaphragm has been closed further for irradiation of the same surface area, in this case exactly the entire irradiated surface of the object, so that a beam 19' is transmitted via a smaller aperture.

The Figure diagrammatically shows drive motors 30 and 32 which serve to drive the diaphragm laminations and each of which is provided with an encoder 34, 36, or is constructed as a step motor. A corresponding drive motor 38 with an encoder 40 for the $\theta$-axis is also shown. In a control mechanism 10 the three motors can be coupled via the encoders and the motor position as well as the control of each of the motors can be controlled. Such a control can be performed independently or directly coupled for each of the motors. In a simplified embodiment, motors can be coupled, for example mechanically. In that case the control system 10 acts more or less as a measuring system for detecting the position of the motors. For example, in a less rigid system, for example the drive motor for the $\theta$-angle is coupled to a first motor of the diaphragm system merely via encoding, a second motor being mechanically coupled to the first diaphragm motor. A more flexible system couples all three motors exclusively via encoding. When mechanically coupled motors are involved, use can also be made of a single motor for several drives. If coupling is realized only via encoding, it is more practical to use separate motors.

The laminations of the described embodiment are identical. However, use can also be made of mutually different laminations, for example laminations having a different radius so that asymmetry in the beam path, for example due to a difference in distance between the front and the rear of the object, viewed along the beam path, can be compensated for.

Figure 3:
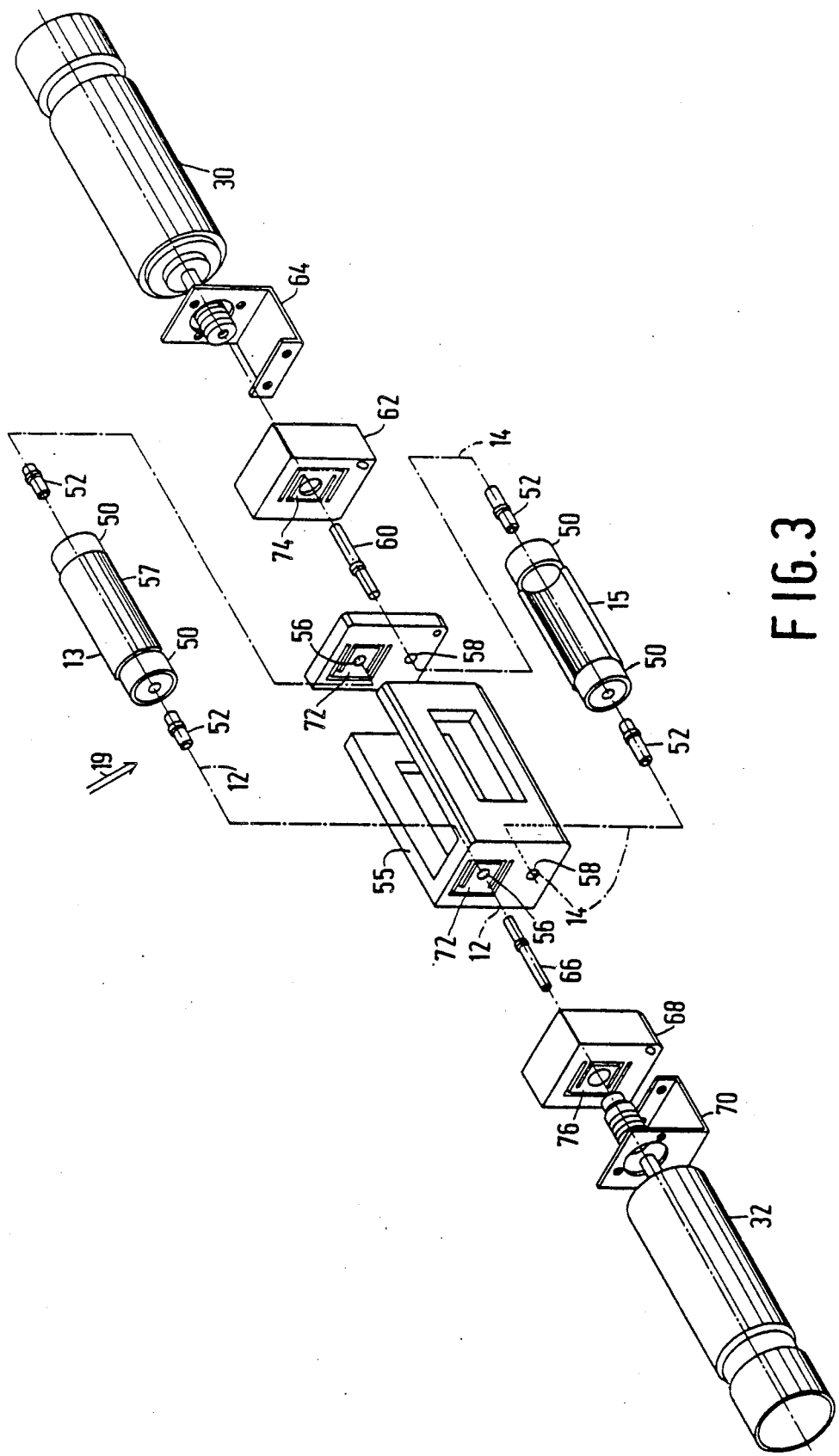

An embodiment of a diaphragm system as shown in FIG. 3 is an example of the construction of an adjustable slit diaphragm with a first lamination 13 and a second lamination 15 which are shown as separate parts for the sake of clarity. Both laminations constitute envelope portions, for example amounting to slightly less than 180°, of cylinders which are rotatable about shafts 12 and 14, respectively, via bushes 50 and coupling pieces 52. The laminations can be mounted in a diaphragm housing 55 by means of the coupling pieces 52 so that the axis of rotation 12 of the lamination 13 coincides with the center of apertures 56 in the housing, and that the axis of rotation 14 of the lamination 15 coincides with the center of apertures 58 in the housing, a concave side of the lamination 13 facing an incident X-ray beam 19 whilst the lamination 15 faces said beam by way of a convex side. A first drive motor 30 is axially coupled to the rotary shaft 12, via a coupling piece 60, a spring member 62 and a support 64, a second drive motor 32 being axially coupled to the rotary shaft 14, via a coupling piece 66, a spring member 68 and a support 70. The spring members 62 and 68 can with a sufficient accuracy of the construction parts also be omitted. The shaft 14 of the lamination 15 is rigidly coupled to the diaphragm housing 55, the shaft 12 of the lamination 13 being coupled to the housing via resilient journals 72 so that it can be adjustedly mounted parallel to the lamination 15 at a strictly defined distance therefrom. Similarly, the lamination 13 may also be rigidly mounted and the lamination 15 may be mounted so as to be resilient. The housing 55, the spring members 62 and 68, and the supports 64 and 70 can be rigidly mounted in the analysis apparatus; in practical cases, all these elements are rigidly connected to the housing 55 and are mounted in the goniometer housing of the apparatus as one unit. The motors as such, and hence the drive shafts for the laminations thereof, are thus coupled to the housing via resilient journals 74 and 76, thus avoiding non-parallelism with respect to the $\theta$-axis and also wear during rotation but the drive shafts can also be rigidly coupled.

I claim:

1. An X-ray analysis apparatus, comprising an X-ray source, an adjustable divergence slit, an angle adjusting mechanism for rotating an object about an $\theta$-axis, and an X-ray detector, wherein the improvement comprises that the adjustable divergence slit comprise two cylindrical X-ray absorbing laminations each being rotatably mounted on their axes, said axes extending parallel to the $\theta$-axis of the angle adjusting device, said axes being situated at a distance which is substantially equal to the cylinder radius of the respective cylindrical laminations, on both sides of a radiation vector extending between the center of the X-ray source and the central point of the object to be irradiated.

2. An X-ray analysis apparatus as claimed in claim 1, wherein one of the X-ray absorbing laminations is disposed so that its concave side faces the X-ray source and the other of the X-ray absorbing laminations is disposed so that its convex side is disposed towards the X-ray source.

3. An X-ray analysis apparatus as claimed in claim 1, characterized in that the X-ray absorbing laminations are rotatable about their axes at mutually equal angular speeds.

4. The X-ray analysis apparatus as claimed in claim 2, wherein the concave cylindrical lamination which faces the X-ray source is disposed on the side of the radiation vector which is located within an angle formed between the X-ray source, the object to be irradiated and the X-ray detector.

5. An X-ray analysis apparatus as claimed in claim 1, characterized in that the rotations of the X-ray absorbing laminations are independently adjustable.

6. An X-ray analysis apparatus as claimed in claim 1, characterized in that by choosing the radius of the laminations for the lamination diaphragm for comparatively small $\theta$-values an acceleration to approximately a factor 10 is adjustable between the angular speed for specimen rotation and for lamination rotation.

7. An X-ray analysis apparatus as claimed in claim 1, characterized in that one of the laminations is provided with an axially extending ridge, the other lamination being provided with an axially extending groove which cooperates with said ridge in order to achieve complete closure, the lamination rotation being synchronous over a final path.

8. An X-ray apparatus as claimed in claim 1, characterized in that a shaft of a first lamination of the divergence slit is rigidly mounted in a lamination housing, a shaft of a second lamination being mounted therein so as to be resilient with respect to the first shaft.

9. An X-ray analysis as claimed in claim 1 characterized in that lamination drive motors are resiliently mounted on a lamination housing.

10. An X-ray analysis apparatus as claimed in claim 8, characterized in that resilient coupling members are provided with a slit spring system.

11. An X-ray analysis apparatus, comprising an X-ray source, an adjustable diversion slit, an angle adjusting mechanism for rotating an object about a $\theta$-axis, and an X-ray detector, wherein the improvement comprises that the adjustable diversion slit comprises two cylindrical X-ray absorbing laminations each mounted on an envelope of respective cylinders, said cylinders being rotatable about axes extending parallel to the $\theta$-axis of the angle adjusting device, and that the rotation of the X-ray absorbing laminations are independently adjustable.

* * * * *